United States Patent [19]

Nadelson

[11] 4,011,344

[45] Mar. 8, 1977

[54] IMINODIMETHYLENE DI-TERT-ALKYLOPHENONES AND PHENOLS

[75] Inventor: Jeffrey Nadelson, Lake Parsippany, N.J.

[73] Assignee: Sandoz, Inc., E. Hanover, N.J.

[22] Filed: June 20, 1975

[21] Appl. No.: 588,789

Related U.S. Application Data

[63] Continuation-in-part of Ser. No. 558,180, March 14, 1975, abandoned, which is a continuation-in-part of Ser. No. 460,891, April 15, 1974, abandoned.

[52] U.S. Cl. .......................... 424/330; 260/501.18; 260/570.9; 260/592; 424/316
[51] Int. Cl.$^2$ ..................... A01N 9/20; C07C 87/28
[58] Field of Search .................. 260/570.9, 501.18; 424/330, 316

[56] References Cited

UNITED STATES PATENTS 3,493,662  2/1970  Duerr ..................... 260/570.9 UX

*Primary Examiner*—Robert V. Hines
*Attorney, Agent, or Firm*—Gerald D. Sharkin; Robert S. Honor; Timothy G. Rothwell

[57] ABSTRACT

Substituted-iminodimethylene-di-tert-alkylophenones, e.g., 4'', 4'''-methyliminodimethylene-dipivalophenone, are prepared by treating a corresponding α-halo-p-tert-alkanoyl toluene with a substituted amine. The phenylcarbinols are prepared from the corresponding phenones and both the phenones and the phenylcarbinols are useful as hypolipidemic agents.

13 Claims, No Drawings

IMINODIMETHYLENE DI-TERT-ALKYLOPHENONES AND PHENOLS

This application is a continuation-in-part of copending application Ser. No. 558,180, filed Mar. 14, 1975 and now abandoned, which in turn is a continuation-in-part of application Ser. No. 460,891, filed Apr. 15, 1974 and now abandoned.

This invention relates to substituted-iminodimethylene-di-tert-alkylophenones and phenylcarbinols. In particular, it relates to substituted-iminodimethylene-di-tert-alkylophenones and corresponding phenylcarbinols, pharmaceutically acceptable salts thereof, and to preparation of the salts and the base forms thereof.

The phenylcarbinols of this invention may be represented by the following structural formula (Ia)

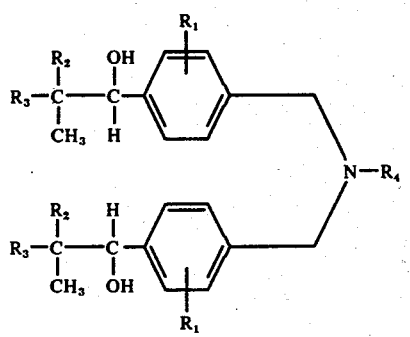

wherein
R$_1$ represents hydrogen, halo having an atomic weight of about 19 to 36, and straight chain lower alkoxy, i.e., straight chain alkoxy having 1 to 4 carbon atoms, e.g., methoxy, ethoxy, and the like, and
R$_2$ and R$_3$ each independently represent alkyl having 1 to 2 carbon atoms, i.e., methyl or ethyl, and
R$_4$ represents lower alkyl having 1 to 4 carbon atoms, e.g., methyl, ethyl, and the like.
and may be prepared from compounds of formula (I), another aspect of this invention,

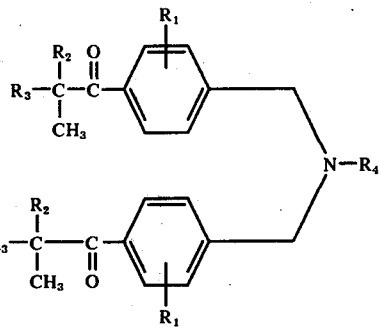

where R$_1$, R$_2$, R$_3$ and R$_4$ are as defined above, by reduction of the latter using either lithium aluminum hydride in ether solvents such as alkyl ethers, e.g., diethyl ether and cyclic ethers such as tetrahydrofuran, or alkali metal borohydide in alcoholic solvents. Alkali metal borohydrides which may be used include sodium borohydride and potassium borohydride whereas the alcoholic solvents include ethanol, propanol, isopropanol and the like. The reduction may be performed at temperatures of from about minus 20° C. to about plus 10° C., preferably 0° C. for about ½ to 3 hours, conveniently 1 hour, but neither the temperature nor the time of reaction are critical.

The compounds of formula (I) are prepared according to the following reaction scheme:

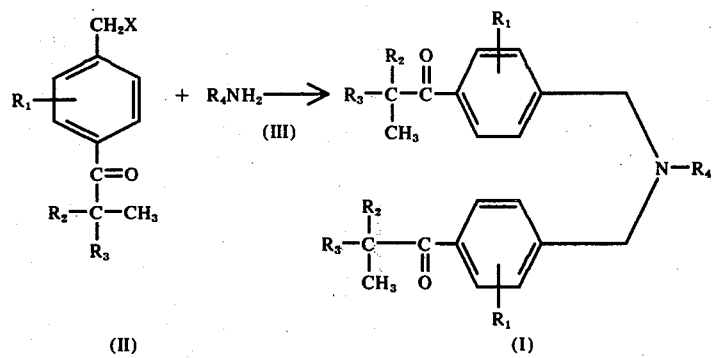

where
X represents chlorine or bromine, and
R$_1$, R$_2$, R$_3$ and R$_4$ are as defined above.

The compounds of formula (I) are prepared by treating a compound of the formula (II) with a compound of the formula (III) in the presence of an inert organic solvent. Although the particular solvent employed is not critical, the preferred solvents include the aromatic hydrocarbons such as benzene, toluene and the like, the halogenated hydrocarbons such as methylenedichloride, chloroform and the like, and the ethers such as tetrahydrofuran or diethyl ether, preferably benzene. The temperature of the reaction is not critical, but it is preferred that the reaction be run from about 25° to 150° C., preferably the reflux temperature of the solvent. The reaction is run from about 10 to 48 hours, preferably from about 20 to 26 hours. The product is recovered using conventional techniques, e.g., crystallization followed by filtration.

The compounds of formula (II) are prepared according to the following reaction scheme:

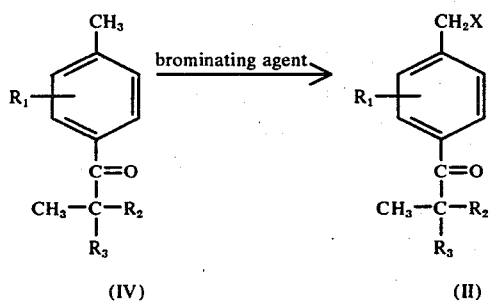

where $R_1$, $R_2$, $R_3$, $R_4$ and X are as defined above.

The compounds of formula (II) are prepared by treating a compound of formula (IV) with a halogenating agent in the presence of an inert organic solvent and free radical initiator. The halogenating agent which can be used is bromine, N-bromosuccinimide, N-bromo phthalamide, N-bromoacetamide, chlorine, N-chlorosuccinimide and the like. The particular agent used is not critical, but N-bromosuccinimide is preferred. In the preferred process, the free radical initiator used is an organic peroxide, especially benzoyl peroxide. The reaction can also be carried out under ultraviolet light. Although the particular solvent used is not critical, the preferred solvents are the halogenated hydrocarbons such as methylenedichloride, chloroform, carbon tetrachloride and the like, although the aromatic hydrocarbons such as benzene can also be employed. The temperature of the reaction is not critical, but reflux temperature of the solvent is preferred. The reaction is run for about 12 to 48 hours; preferably about 18 to 25 hours. The product is recovered by conventional techniques, e.g., crystallization.

Many of the compounds of formula (III) and (IV) are known and may be prepared by methods described in the literature. The compounds of formula (III) and (IV) not specifically disclosed may be prepared by analogous methods from known starting materials.

The compounds of formula (Ia) exist in the form of diastereo and optically active isomers and separation and recovery of the isomers may be readily accomplished employing conventional techniques, such as fractional crystallization.

The compounds of formulae (I) and (Ia) are useful because they possess pharmaceutical activity in animals as hypolipidemic agents, particularly as hyperlipoproteinemic agents as indicated by the fall in cholesterol and triglyceride levels in male albino Wistar rats weighing 110–130 g. initially. The rats are maintained on drug-free laboratory chow diet for seven days and then divided into groups of 8 to 10 animals. Each group with the exception of the control is then given orally 120 milligrams per kilogram of body weight per diem of the compound for six days. At the end of this period, the animals are anesthetized with sodium hexobarbital and bled from the carotid arteries. Serum or plasma samples are collected, and 1.0 ml. samples of the serum are added to 9.0 ml. redistilled isopropanol. Two autoanalyzer cupsful of a mixture of zeolite-copper hydroxide and Lloydds reagent (Kessler, G., and Lederer, H., 1965, Technicon Symposium, Mediad Inc., New York, (345–347) are added, and the mixture is shaken for 1 hour. Cholesterol and triglyceride levels are determined simultaneously on the same sample by Technicon N 24 A (cholesterol) and N-78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control triglyceride levels.

For such usage, the compounds (I) and (Ia) may be combined with a pharmaceutically acceptable carrier or adjuvant and may be administered orally or parenterally as such or admixed with conventional pharmaceutical carriers. They may be administered in such forms as tablets, dispersible powders, granules, capsules, syrups, and elixirs and parenterally as solutions, suspensions, dispersions, emulsions and the like, e.g., a sterile injectable aqueous solution. The dosage will vary depending upon the mode of administration utilized and the particular compound employed.

The compounds of formulae (I) and (Ia) may be similarly administered in the form of their non-toxic pharmaceutically acceptable salts. Such salts possess the same order of activity as the free base and are readily prepared by reacting the base with an appropriate acid by reacting the base with an appropriate acid by conventional techniques and, accordingly, are included within the scope of this invention. Representative of such salts are the mineral acid salts, e.g., hydrochloride, hydrobromide, sulfate and the like, and the organic acid salts such as succinate, benzoate, maleate and the like.

The hypolipidemic effective dosage of these active compounds in the alleviation of lipidemia may vary depending on the particular compound employed and the severity of the condition being treated. However, in general, satisfactory results are obtained when the compounds of formulae (I) and (Ia) are administered at a daily dosage of from about 4.0 milligrams to about 250 milligrams per kilogram of animal body weight, preferably given in divided doses two to four times a day, or in sustained release form. For most large mammals, the total daily dosage is from about 300 milligrams to about 2000 milligrams. Dosage forms suitable for internal use comprise from about 75.0 to about 1000 milligrams of the active compound in intimate admixture with a solid or liquid pharmaceutically acceptable carrier or diluent.

A representative formulation suitable for oral administration 2 to 4 times a day for the treatment of lipidemia is a capsule prepared by standard encapsulating techniques which contains the following:

| Ingredients | Weight (mg.) |
| --- | --- |
| 4″,4‴-methyliminodimethylene-di-pivalophenone | 150 |
| inert solid diluent (starch, lactose, kaolin) | 300 |

A preferred aspect of this invention concerns compounds (I) and (Ia) wherein $R_4$ represents methyl, $R_2$ and $R_3$ represent methyl or $R_2$, $R_3$ and $R_4$ all represent methyl.

EXAMPLE 1

α-bromo-p-pivaloyl toluene

To a suspension of 28.5 g. (1.17 g. atoms) magnesium turnings in 150 ml. tetrahydrofuran under a nitrogen atmosphere there is added 10 ml. of 4-bromo toluene (1.17 mole) in 650 ml. dry tetrahydrofuran; the reaction is started and the remainder of the bromo toluene solution is added dropwise at a rate that maintains a moderate reflux. After the addition is complete, the mixture is refluxed for an additional 1½ hours. The resulting Grignard solution is added dropwise to a cold solution of 128.0 g. pivaloyl chloride (1.06 mole) in 500 ml. dry tetrahydrofuran at a rate that maintains the temperature at 0° to −5° C. The solution is stirred for an additional 1½ hours at 0° C. and then at room temperature for 18 hours. The mixture is then cooled to 0° C. and hydrolyzed by the addition of 100 ml. 2N hydrochloric acid. The layers are separated and 200 ml. of ether is added to the organic phases which is then washed respectively with 100 ml. 2N hydrochloric acid, 100 ml. 10% sodium bicarbonate solution, and 100 ml. saturated sodium chloride. The resulting layer is dried over anhydrous sodium sulfate, filtered, and the solvent is removed in vacuo to give p-pivaloyl toluene (b.p. 80° to 84° C./0.7 mm, $n_c^{21}$ 1.5108). A mixture of 156.3 g. (0.886 mole) of the resulting p-pivaloyl toluene is then added to 157.8 g. (0.886 mole) N-bromosuccinimide, 4.0 g. (0.016 mole) benzoyl peroxide and 150 ml. carbon tetrachloride and heated at reflux for 18 hours. The mixture is cooled and filtered and the resulting oil is distilled in vacuo to give α-bromo-p-pivaloyl toluene (b.p. 124°–132° C/0.7 mm, $n_D^{22}$ 1.5546-V.P.C. 96% monobromo 4%-dibromo).

Following the above procedure and using in place of 4-bromo-toluene equivalent amounts of:
a. 4-bromo-2-chlorotoluene,
b. 4-bromo-2-methoxytoluene, or
c. 4-bromo-2-fluorotoluene,
there is obtained
a. α-bromo-2-chloro-4-pivaloyl toluene,
b. α-bromo-2-methoxy-4-pivaloyl toluene, or
c. α-bromo-2-fluoro-4-pivaloyl toluene, respectively.

EXAMPLE 2

4″,4‴-methyliminodimethylene-dipivalophenone

A mixture of 300 ml. benzene and anhydrous methylamine is added dropwise to 6.0 grams (0.235 mole) of α-bromo-p-pivaloyl toluene in 600 ml. of benzene and anhydrous methylamine is bubbled through the solution. After the addition is complete, the methylamine flow is continued and the mixture is refluxed for 6 hours. The methylamine flow is ceased and the mixture is refluxed for an additional 18 hours, cooled in ice and the solvents evaporated in vacuo. The resulting residue is treated with water and diethyl ether and the layers are separated and the water is extracted with diethyl ether. The combined diethyl ether layers are washed with 2N hydrochloric acid (twice) and the acid layers are cooled and made basic by addition of solid sodium hydroxide and extracted with ether. The ether is washed with water and brine, dried over anhydrous magnesium sulfate, filtered and evaporated in vacuo. The residue is dissolved in ethanol and treated with anhydrous hydrochloric acid. The mixture is cooled in ice and the resulting crystals are filtered and washed with cold ethanol to give 4″,4‴-methyliminodimethylenedipivalophenone hydrochloride, m.p. 238°–239° C.

Following the above procedure and using in place of α-bromo-p-pivaloyl toluene an equivalent amount of
a. α-bromo-2-chloro-4-pivaloyl toluene,
b. α-bromo-2-methoxy-4-pivaloyl toluene, or
c. α-bromo-2-fluoro-4-pivaloyl toluene,
there is obtained in hydrochloride salt form
a. 3″,3‴-dichloro-4″,4‴-methyliminodimethylenedipivalophenone,
b. 3″,3‴-dimethoxy-4″,4‴-methyliminodimethylenedipivalophenone, or
3″,3‴-difluoro-4″,4‴-methyliminodimethylenedipivalophenone, m.p. 205° to 206.5° C., respectively.

Again following the above procedure and using in place of methylamine in equivalent amount of ethylamine, there is obtained 4″,4‴-ethyliminodimethylenedipivalophenone hydrochloride, m.p. 106° to 108° C.

The 4″,4‴-methyliminodimethylene-dipivalophenone hydrochloride of this example is an effective hypolipidemic agent when orally administered to an animal suffering from lipidemia at a dosage of 150 mg. four times per day.

EXAMPLE 3

4,4′-(methyliminodimethylene)bis(α-t-butylbenzyl alcohol)

A suspension of 3.8 g. of lithium aluminum hydride (0.105 mole) in 40 ml. of dry tetrahydrofuran is cooled to 0° C. and treated by the dropwise addition of a solution of 10 g. of 4″,4‴-methyl-iminodimethylene-dipivalophenone (0.0264 mole) in 100 ml. dry tetrahydrofuran. After the addition is complete, the mixture is stirred 1 hour at 0° C. and then decomposed with ethyl acetate, 2N sodium hydroxide and water (6:2:3 ml/g. lithium aluminum hydride). Magnesium sulfate is added to the mixture and then filtered. The filtrate is evaporated in vacuo and the residue is recrystallized from ethyl ether containing some ethanol to give 4,4′-(methyliminodimethylene)bis(α-t-butylbenzyl alcohol); m.p. 140°–142.5° C.

When a sodium borohydride-ethyl alcohol reduction system is utililzed in place of the lithium aluminum hydridetetrahydrofuran system as indicated above, 4,4′-(methyliminodimethylene)bis(α-t-butylbenzyl alcohol) is again obtained.

When the above-detailed procedure of this example is performed and in place of 4″,4‴-methyliminodimethylene dipivalophenone there is used
a. 3″,3‴-dichloro-4″,4‴-methyliminodimethylene dipivalophenone,
b. 3″,3‴-dimethoxy-4″,4‴-methyliminodimethylene dipivalophenone, or
c. 3″,3‴-difluoro-4″,4‴-methyliminodimethylene dipivalophenone,
there is obtained
a. 4,4′-(methyliminodimethylene)bis(α-t-butyl-3-chlorobenzyl alcohol);
b. 4,4′-(methyliminodimethylene)bis(α-t-butyl-3-methoxybenzyl alcohol); or
c. 4,4′-methyliminodimethylene)bis(α-t-butyl-3-fluorobenzyl alcohol), respectively.

What is claimed is:
1. A compound of the formula:

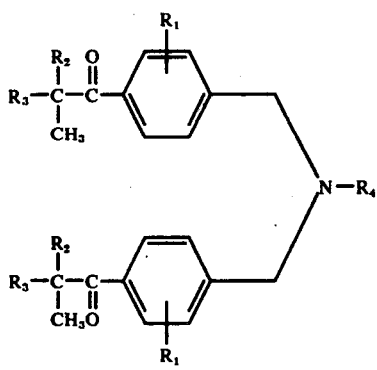

wherein

R₁ represents hydrogen, halo having an atomic weight of about 19 to 36 or straight chain lower alkoxy, and R₂ and R₃ each independently represent lower alkyl having 1 to 2 carbon atoms, and R₄ represents lower alkyl having 1 to 4 carbon atoms, or a pharmaceutically acceptable salt thereof.

2. A compound of the formula:

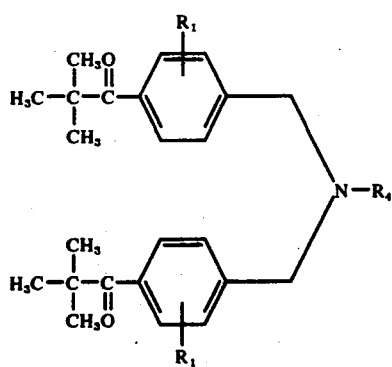

where $R_1$ and $R_4$ are as defined in claim 1, or a pharmaceutically acceptable salt thereof.

3. A compound of the formula:

$R_1$, and $R_2$ and $R_3$ are defined in claim 1.

4. The compound of claim 1 which is 4'',4'''-methyliminodimethylene-dipivalophenone hydrochloride.

5. The compound of claim 1 which is 4'',4'''-methyliminodimethylene-dipivalophenone.

6. The compound of claim 1 which is 4'',4'''-ethyliminodimethylene-dipivalophenone hydrochloride.

7. The compound of claim 1 which is 4'',4'''-ethyliminodimethylene-dipivalophenone.

8. The compound of claim 1 which is 3'',3'''-dimethoxy-4'',4'''-methyliminodimethylene-dipivalophenone hydrochloride.

9. The compound of claim 1 which is 3'',3'''-dimethoxy-4'',4'''-methyliminodimethylene-dipivalophenone.

10. The compound of claim 1 which is 3'',3'''-difluoro-4'',4'''-methyliminodimethylene-dipivalophenone hydrochloride.

11. The compound of claim 1 which is 3'',3'''-difluoro-4'',4'''-methyliminodimethylene-dipivalophenone.

12. A pharmaceutical composition in unit dosage form useful as a hypolipidemic agent comprising a compound of claim 1 and a pharmaceutically acceptable diluent or carrier therefor said compounds being present in an amount of from about 75.0 milligrams to about 1000 milligrams.

13. A method of treating lipidemia which comprises administering to a mammal in need of said treatment a hypolipidemic effective amount of a compound of claim 1.

* * * * *